(12) United States Patent
Han et al.

(10) Patent No.: US 8,890,121 B1
(45) Date of Patent: Nov. 18, 2014

(54) INTEGRATED NANOWIRE/NANOSHEET NANOGAP AND NANOPORE FOR DNA AND RNA SEQUENCING

(71) Applicant: International Business Machines Corporation, Armonk, NY (US)

(72) Inventors: Shu-Jen Han, Cortlandt Manor, NY (US); Ajay K. Royyuru, Congers, NY (US); Gustavo A. Stolovitzky, Riverdale, NY (US); Deqiang Wang, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 8 days.

(21) Appl. No.: 13/887,804

(22) Filed: May 6, 2013

(51) Int. Cl.
*H01L 29/06* (2006.01)

(52) U.S. Cl.
USPC ............... 257/39; 257/27; 257/192; 435/10; 435/49; 436/2; 436/6

(58) Field of Classification Search
USPC .............................. 257/39, 197; 438/10, 49
See application file for complete search history.

(56) References Cited

U.S. PATENT DOCUMENTS

| | | | | |
|---|---|---|---|---|
| 5,798,042 | A * | 8/1998 | Chu et al. | 210/490 |
| 6,627,067 | B1 * | 9/2003 | Branton et al. | 205/778 |
| 7,468,271 | B2 | 12/2008 | Golovchenko et al. | |
| 2009/0136958 | A1 | 5/2009 | Gershow et al. | |
| 2011/0120868 | A1 | 5/2011 | Lindsay et al. | |
| 2011/0279125 | A1 | 11/2011 | Bedell et al. | |

OTHER PUBLICATIONS

D. J. Branton et al., "The potential and challenges of nanopore sequencing," Nature biotechnology, vol. 26, No. 10, 2008, pp. 1146-1153.
X. Guo et al., "Conductivity of a single DNA duplex bridging a carbon nanotube gap," Nature Nanotechnology, vol. 3, 2008, pp. 163-167.
X. Guo et al., "Covalently Bridging Gaps in Single-Walled Carbon Nanotubes with Conducting Molecules," Science, vol. 311, No. 5759, Jan. 20, 2006, pp. 356-359.
A. Afzali-Ardakani et al "Integrated Carbon Nanotube Field Effect Transistor and Nanochannel for Sequencing," U.S. Appl. No. 13/690,963, filed Nov. 30, 2012.
A. D. Franklin et al., "Device for Electrical Characterization of Molecules using CNT-Nanoparticle-Molecule-Nanoparticle-CNT Structure," U.S. Appl. No. 13/674,492, filed Nov. 12, 2012

* cited by examiner

*Primary Examiner* — Dung A. Le
(74) *Attorney, Agent, or Firm* — Cantor Colburn LLP; Vazken Alexanian

(57) ABSTRACT

A technique is provided for base recognition in an integrated device is provided. A target molecule is driven into a nanopore of the integrated device. The integrated device includes a nanowire separated into a left nanowire part and a right nanowire part to form a nanogap in between, a source pad connected to the right nanowire part, a drain pad connected to the left nanowire part, and the nanopore. The source pad, the drain pad, the right nanowire part, the left nanowire part, and the nanogap together form a transistor. The nanogap is part of the nanopore. A transistor current is measured while a single base of the target molecule is in the nanogap of the nanopore, and the single base affects the transistor current. An identity of the single base is determined according to a change in the transistor current.

3 Claims, 9 Drawing Sheets

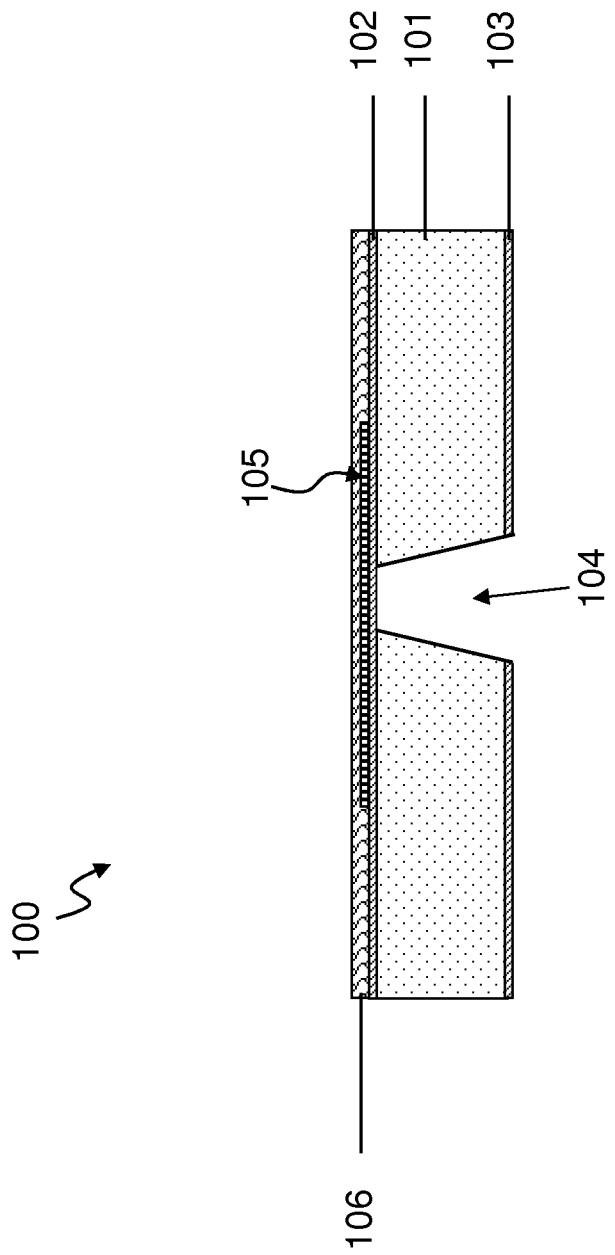

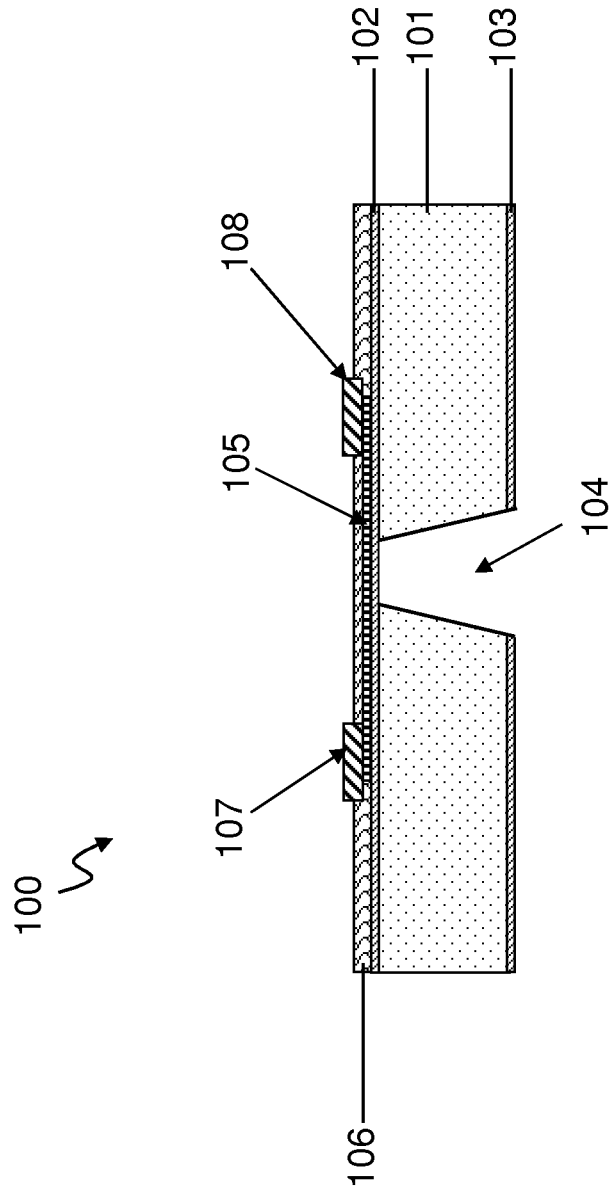

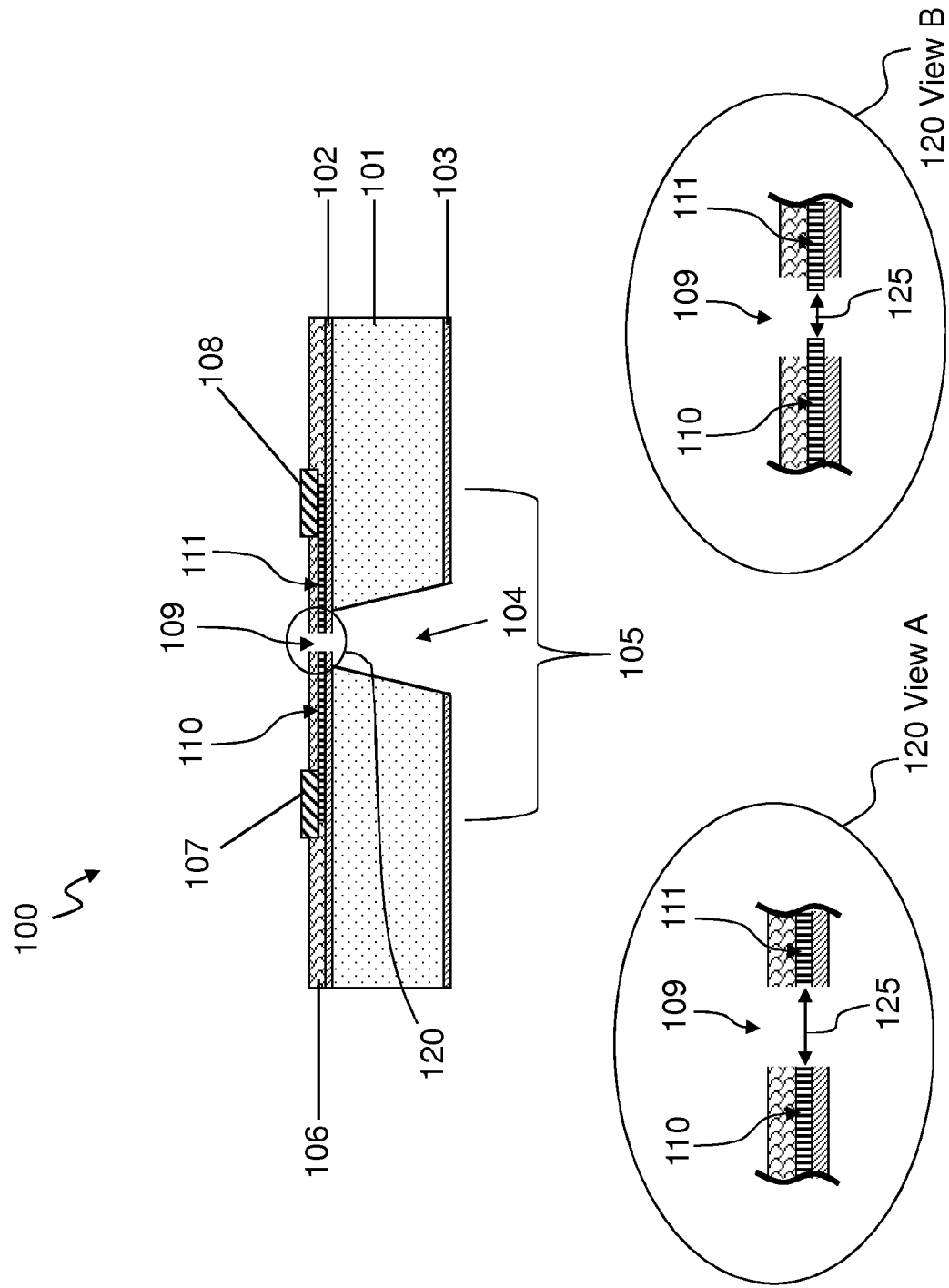

INTEGRATED NANOWIRE/NANOSHEET NANOGAP AND NANOPORE FOR DNA AND RNA SEQUENCING

BACKGROUND

The present invention relates generally to nanodevices, and more specifically, to sequencing using an integrated nanowire/nanosheet nanogap and nanopore device.

Nanopore sequencing is a method for determining the order in which nucleotides occur on a strand of deoxyribonucleic acid (DNA). A nanopore (also referred to a pore, nanochannel, hole, etc.) can be a small hole in the order of several nanometers in internal diameter. The theory behind nanopore sequencing is about what occurs when the nanopore is submerged in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

The DNA can be driven through the nanopore by using various methods, so that the DNA might eventually pass through the nanopore. The scale of the nanopore can have the effect that the DNA may be forced through the hole as a long string, one base at a time, like thread through the eye of a needle. Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/human genome.

SUMMARY

According to one embodiment, a method for base recognition in an integrated device is provided. A target molecule is driven into a nanopore of the integrated device. The integrated device includes a nanowire separated into a left nanowire part and a right nanowire part to form a nanogap in between, a source pad connected to the right nanowire part, a drain pad connected to the left nanowire part, and the nanopore. The source pad, the drain pad, the right nanowire part, the left nanowire part, and the nanogap together form a transistor. The nanogap is part of the nanopore. A transistor current is measured while a single base of the target molecule is in the nanogap of the nanopore, and the single base affects the transistor current. An identity of the single base is determined according to a change in the transistor current.

According to one embodiment, a method for base recognition in an integrated device is provided. A target molecule is driven into a nanopore of the integrated device. The integrated device includes a nanosheet separated into a left nanosheet part and a right nanosheet part to form a nanogap in between, a source pad connected to the right nanosheet part, a drain pad connected to the left nanosheet part, and the nanopore. The source pad, the drain pad, the right nanosheet part, the left nanosheet part, and the nanogap together form a transistor. The nanogap is part of the nanopore. A transistor current is measured while a single base of the target molecule is in the nanogap of the nanopore, and the single base affects the transistor current. An identity of the single base is determined according to a change in the transistor current.

According to one embodiment, an integrated device for base recognition is provided. The integrated device includes a nanopore in which to drive a target molecule, and a transistor. The transistor includes a nanowire or nanosheet separated into a left nanowire part and a right nanowire part to form a nanogap in between, a source pad connected to the right nanowire part, and a drain pad connected to the left nanowire part. The nanogap is part of and aligned to the nanopore. A transistor current is measured while a single base of the target molecule is in the nanogap of the nanopore, and the single base affects the transistor current. An identity of the single base is determined according to a change in the transistor current.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIGS. 1A through 1F illustrate cross-sectional views of fabricating an integrated nanowire/nanosheet nanogap field effect transistor (FET) and nanopore device according to an embodiment, in which:

FIG. 1A is a cross-sectional view of a substrate with top and bottom electrically insulating films;

FIG. 1B is a cross-sectional view of a backside cavity etched into the bottom electrically insulating film through the electrically insulating substrate to the top electrically insulating film;

FIG. 1C is a cross-sectional view of a nanowire/nanosheet placed on top of the top electrically insulating film to be positioned above the cavity;

FIG. 1D is a cross-sectional view of an electrically insulating film deposited on top of both the top electrically insulating film and the nanowire/nanosheet to cover them both;

FIG. 1E is a cross-sectional view of an electrode/drain and electrode/source deposited onto the nanowire/nanosheet; and FIG. 1F is a cross-sectional view of forming a nanopore through the top and bottom electrically insulating films and through the nanowire/nanosheet.

DETAILED DESCRIPTION

Embodiments introduce a method and device to integrate a nanowire/nanosheet nanogap field-effect transistor (nanowire/nanosheet-nanogap-FET) and a nanopore for DNA/RNA sequencing. Single stranded or double stranded DNA/RNA molecules can be pulled through the nanogap and nanopore which can guide the movement of DNA/RNA molecule. The nanowire/nanosheet-nanogap-FET can read the nucleotide information inside the nanogap when the DNA/RNA molecule moves through the nanogap and nanopore.

Currently, different methods are employed to control the trap, ratchet the long DNA/RNA, and sense single nucleotide information. Those methods have not realized the DNA/RNA sequencing in low cost and short time with high accuracy.

Embodiments integrate the nanowire/nanosheet-nanogap-FET and nanopores together as sensors to read the nucleotide information when the DNA/RNA molecule is moving through the nanogap and nanopore.

According to an embodiment, FIGS. 1A through 1F illustrate cross-sectional views of fabricating an integrated device 100, which integrates a nanowire/nanosheet nanogap field effect transistor (FET) and nanopore for DNA/RNA sequencing.

Figure 1A:
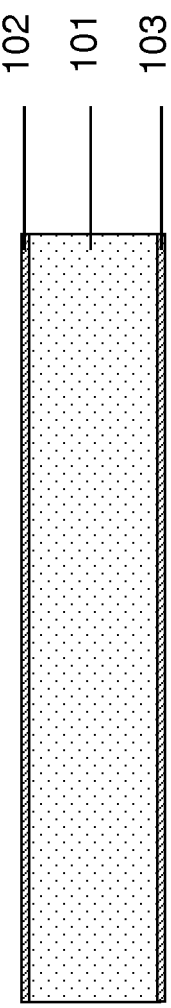

In FIG. 1A, an electrically insulating substrate 101 is shown. The electrically insulating substrate 101, e.g., may be silicon. Electrically insulating films 102 and 103 are disposed above and beneath the electrically insulating substrate 101.

The electrically insulating films 102 and 103 may be hafnium oxide, silicon nitride, etc. The respective thicknesses of the electrically insulating films 102 and 103 may each be few nanometers (e.g., 2, 3, etc.) to tens of nanometers.

Figure 1B:
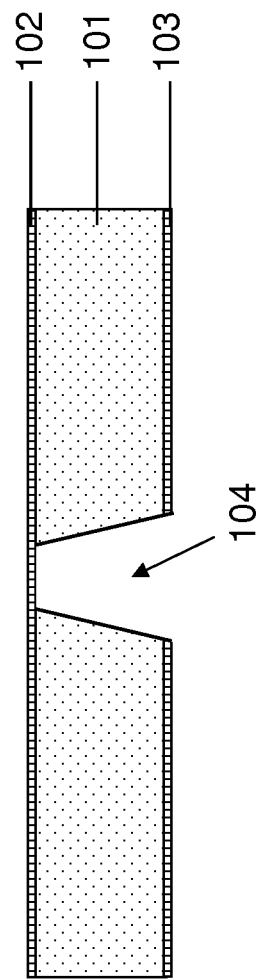

As shown in FIG. 1B, a backside cavity 104 is etched into the electrically insulating film 103 through the electrically insulating substrate 101 stopping at the electrically insulating film 102. The cavity 104 can be fabricated by standard semiconductor processes, like wet etch tetramethylammonium hydroxide (TMAH), potassium hydroxide (KOH), etc.

Figure 1C:
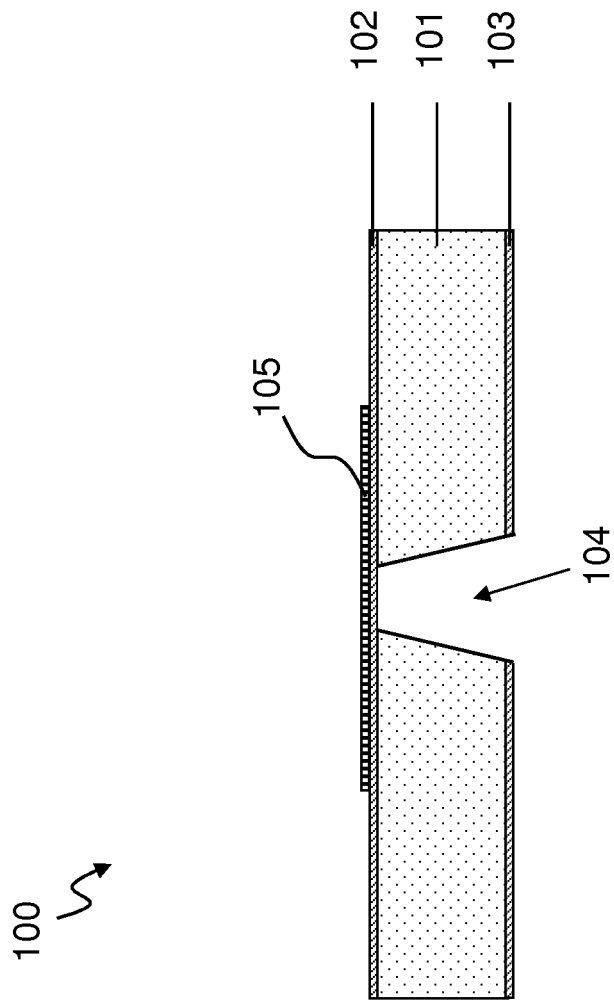

In FIG. 1C, a nanowire/nanosheet 105 is placed on top of the electrically insulating film 102 to be positioned above the cavity 104. The element 105 may be a nanowire or a nanosheet in accordance with embodiments. The nanowires may be silicon nanowires, single or multi-wall CNT (carbon nanotubes), and other semiconductor nanowires. The diameter of nanowires can be 1 to a few nanometers. The nanosheet may be single or multi-layer graphene, a silicon layer, and other semiconductor layers. The thickness of the nanosheets may be 0.3 to a few nanometers thick. The width of nanosheets may be a few to tens of nanometers wide.

In FIG. 1D, an electrically insulating film 106 is deposited on top of both the electrically insulating film 102 and the nanowire/nanosheet 105 to cover them both. The electrically insulating film 106 may be grown with atomic layer deposition to control the accuracy of thickness. The electrically insulating film 106 may be silicon dioxide, aluminum oxide, etc. The thickness of the electrically insulating film 106 may be a few to tens of nanometers thick.

A portion of the electrically insulating film 106 above both the left side and right side of the nanowire/nanosheet 105 is etched away to leave an open left portion and an open right portion. This results in the open left portion and open right portion respectively exposing the left and right sides of the nanowire/nanosheet 105. (Note that e-beam or optical lithography and lift-off processes can be employed to pattern the electrodes 107 and 108.) In FIG. 1E, an electrode/drain 107 is deposited onto the nanowire/nanosheet 105 via the left open portion, and an electrode/source 108 is deposited onto the nanowire/nanosheet 105 via the right open portion. The electrodes 107 and 108 are (metal) contacts physically and electrically connected to the nanowire/nanosheet 105.

FIG. 1F illustrates forming a nanopore 109 through the electrically insulating film 106, through the nanowire/nanosheet 105, and through the electrically insulating film 102. The nanowire/nanosheet 105 is broken to form a nanogap which results in two nanowire/nanosheet parts 110 and 111 of the nanowire/nanosheet 105. Note that the nanopore 109 may be a nanochannel/nanoslit.

In FIG. 1F, the nanopore 109 may be a single or double conical shape nanometer pore including the nanogap in the nanowire/nanosheet 105 (i.e., between part 110 and part 111), which can be fabricated by a reactive ion etch method, transmission electron microscopy (TEM), and helium ion microscopy (HIM). At the same time, the nanogap between nanowire/nanosheet 105 is formed when the nanopore 109 is fabricated.

At the bottom left and right, FIG. 1F illustrates an enlarged views 120 of the nanopore 109 to highlight the nanogap 125. In both view A and view B of enlarged views 120, the nanogap 125 separates the nanowire/nanosheet 105 into two parts 110 and 111. The nanogap 125 can be few nanometers, e.g., 2 to 7 nm. In view A, the nanogap 125 is approximately the same gap distance (from left to right) as the nanopore 109.

In view B, the nanogap 125 is a smaller gap distance than the nanopore 109. For example, the nanogap 125 may be 1 or 2 nanometers smaller in distance (from left to right) than the nanopore 109, which provides a tighter and closer fit to the size of the base of the DNA molecule and/or RNA molecule (e.g., a target molecule 211 shown in FIG. 2) being sequenced, thus controlling the motion of the DNA/RNA molecule traversing through the nanopore 109 and nanogap 125. In view B, more voltage (of a voltage source 217 shown in FIG. 2) is needed to generate a larger electric field to move the DNA/RNA molecule through the nanopore 109 and nanogap 125 (as compared to view A in which the nanopore 109 and nanogap 125 have an equal distance (from left to right)).

As noted above, the diameter of nanowires can be 1 to few nanometers. The nanopore will be underneath of the nanogap. The nanogap will break the nanowire 105 into two parts 110 and 111. The thicknesses of nanosheets can 0.3 to few nanometers. The width of nanosheets can few to tens of nanometers. The nanogap will break the nanosheet 105 into two parts 110 and 111 as well. There is no connection between two parts 110 and 111. In the meanwhile, the nanopore/nanoslit is underneath the nanogap.

Figure 2:
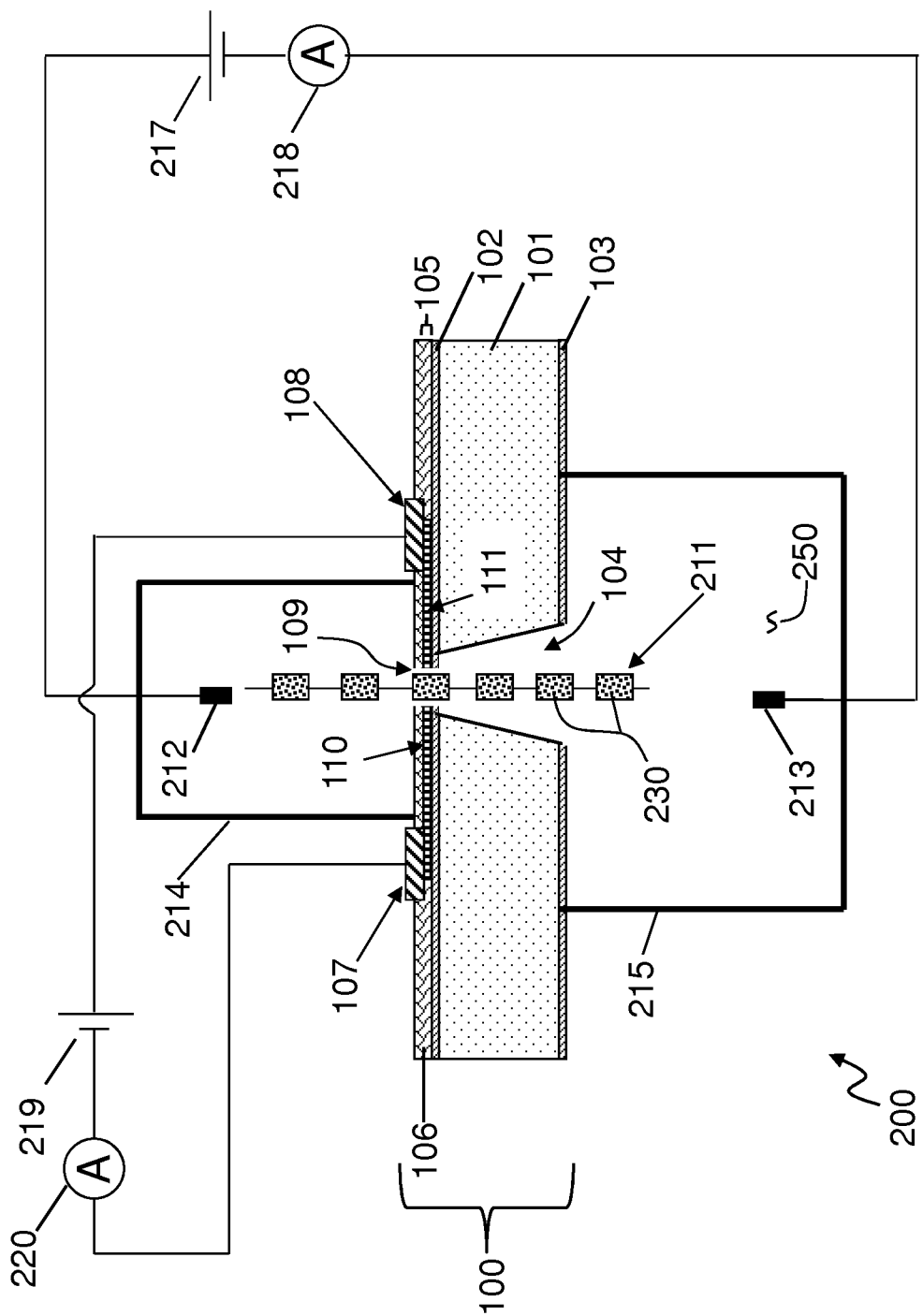
FIG. 2 is a cross-sectional view of a system with the integrated nanowire/nanosheet nanogap field effect transistor (FET) and nanopore device according to an embodiment.

FIG. 2 illustrates the setup for a system 200 with the integrated nanowire/nanosheet nanogap field effect transistor (FET) and nanopore device 100 according to an embodiment. As discussed above, the integrated device 100 includes the electrically insulating substrate 101, and electrically insulating films 102, 103, and 106. The backside cavity 104 forms a suspended membrane making up the nanopore 109 and nanogap 125. The suspended membrane (having the nanopore 109) includes the electrically insulating film 102, the nanowire/nanosheet 105 shown as the left part 110 and right part 111, and the electrically insulating film 106. The suspended membrane is suspended (i.e., hanging) over the cavity 104. The electrodes 107 and 108 are metal contact pads, which may be any metal.

In the system 200, a top reservoir 214 is attached and sealed to the top of the integrated device 100, and a bottom reservoir 215 is attached and sealed to the bottom of the integrated device 100. Electrode 212 is in the top reservoir 214, and electrode 213 is in the bottom reservoir 215. Electrodes 212 and 213 may be silver/silver chloride, or platinum. The reservoirs 214 and 215 are the inlet and outlet respectively for buffer solution 250, and reservoirs 214 and 215 hold the DNA and/or RNA samples for sequencing. The buffer solution 250 is an electrically conductive solution (such as an electrolyte) and may be a salt solution such as NaCl.

The system 200 shows a target molecule 211, which is the molecule being analyzed and/or sequenced. As an example DNA sample, the system 200 may include single stranded or double stranded DNA molecule 211, which is passing through the nanopore 109 and the nanowire/nanosheet 105 (separated into left nanowire/nanosheet part 110 and right nanowire/nanosheet part 111 forming the nanogap 125). The DNA molecule 211 has bases 230 (A, G, C, and T) represented as blocks.

The DNA molecule 211 is pulled through the nanopore 109 (and nanowire/nanosheet nanogap 125) by a vertical electrical field generated by the voltage source 217. When voltage is applied to electrodes 212 and 213 by the voltage source 217, the voltage generates the electric field (between reservoirs 214 and 215) that controllably (e.g., by turning on and off the voltage source 217) drives the DNA molecule 211 into and through the nanopore 109 (and nanogap 125). Also, the voltage of the voltage source 217 can produce the gate bias for nanowire/nanosheet nanogap FET device 100. The voltage across the nanogap 125 and nanopore 109 from the voltage source 217 can be the gate for controlling the device. Metal pads (electrodes) 107 and 108 are the drain and source respectively for the nanowire/nanosheet nanogap FET device. Voltage applied by voltage source 219 to electrodes 107 and 108 also builds the electrical field the left part 110 and right part 111, which can hold the base 230 in the nanogap 125.

Ammeter 218 monitors the ionic current change when DNA (or RNA) molecule 211 goes through 209. The ionic current (measured by the ammeter 218) flows through electrode 212, into the buffer solution 250, through the nanopore 109 (to interact with the base 230 when the target molecule 211 is present in the nanopore 109), out through the electrode 213. Voltage generated by the voltage source 219 produces the voltage between sources 108 and drain 107. An ammeter 220 monitors the source-drain transistor current from nanowire/nanosheet nanogap FET transistor (e.g., from right nanowire/nanosheet part 111 through the buffer solution 250 to the left nanowire/nanosheet part 110) to detect nucleotide (i.e., bases) information when the DNA/RNA molecule 211 passes through the nanowire/nanosheet nanogap 125 and nanopore 109.

For example, when a base (and/or complimentary bases) 230 is in the nanopore 109 (between the nanogap of the nanowire/nanosheet 105) and when voltage is applied by the voltage source 219, source-drain transistor current flows to source 108, into the right nanowire/nanosheet part 111 (of the nanowire/nanosheet 105), into the buffer solution 250 (between nanogap) to interact with the base 230 positioned therein, into left nanowire/nanosheet part 110 (of the nanowire/nanosheet 105), out through the drain 107, and to the ammeter 220. The ammeter 220 is configured to measure the change in source-drain current when each type of base 230 is present in the nanogap 125 (between the left and right parts 110 and 111) and when no base 230 (of the DNA molecule 211) is present. The respective bases 230 are determined by the amplitude of the source-drain transistor current when each respective base in present in the nanogap 125 of the nanopore 109.

Figure 3:
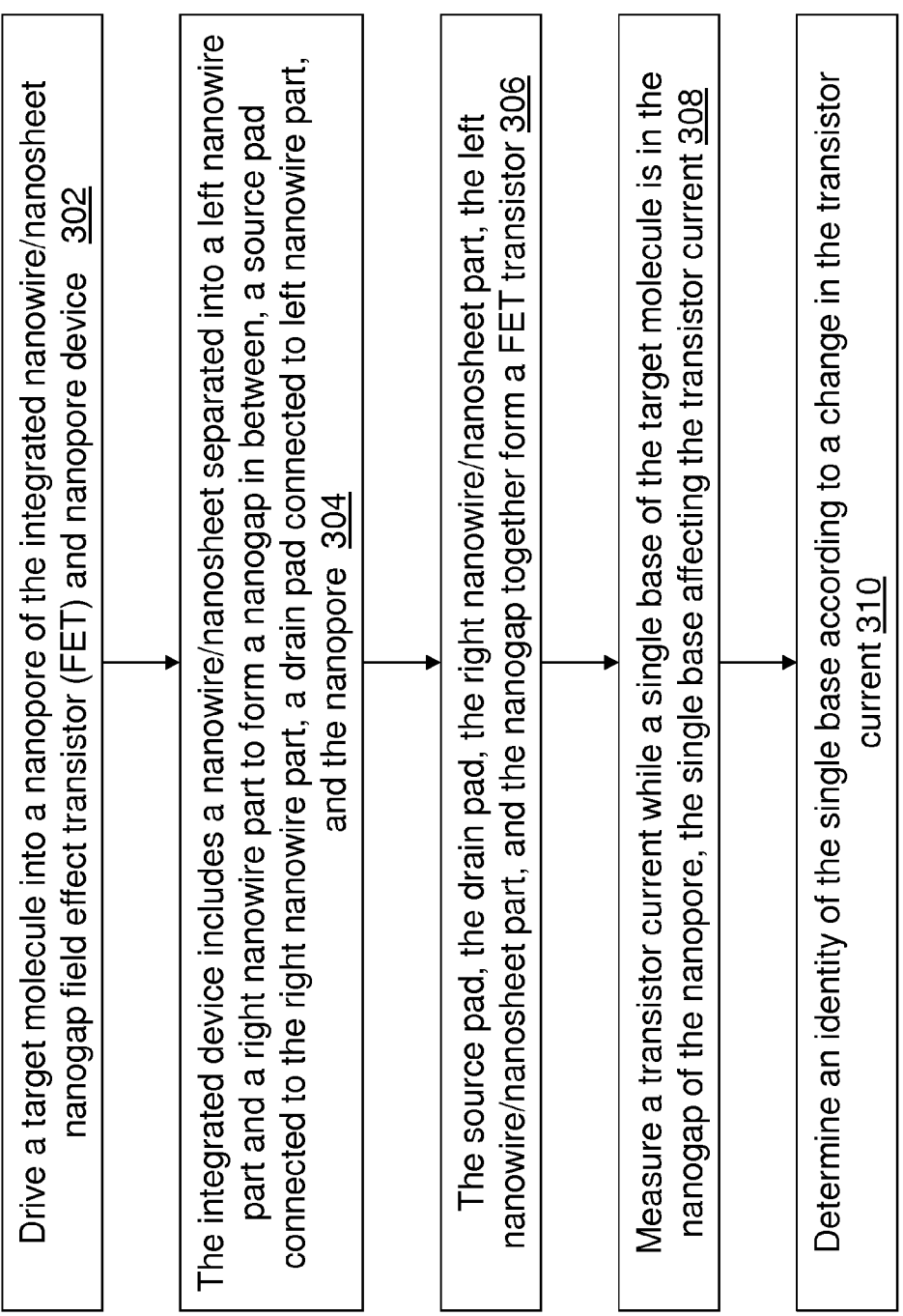
FIG. 3 is a method for base recognition in the integrated nanowire/nanosheet nanogap field effect transistor (FET) and nanopore device according to an embodiment.

FIG. 3 is a method for base recognition in the integrated nanowire/nanosheet 105 nanogap field effect transistor (FET) and nanopore device 100 according to an embodiment. Reference can be made to FIGS. 1 and 2 (along with FIG. 4 discussed below).

Voltage of the voltage source 217 generates a vertical electric field to drive the target molecule 211 (from the top reservoir 214) into the nanopore 109 of the integrated nanowire/nanosheet nanogap field effect transistor (FET) and nanopore device 100 at block 302.

The integrated nanowire/nanosheet nanogap field effect transistor (FET) and nanopore device 100 includes the nanowire/nanosheet 105 separated into a left nanowire/nanosheet part 110 and a right nanowire/nanosheet part 111 to form the nanogap 125 in between, the source pad 108 (electrically and physically) connected to the right nanowire/nanosheet part 111, the drain pad 107 (electrically and physically) connected to left nanowire/nanosheet part 110, and the nanopore 109 at block 304.

The source pad 108, the drain pad 107, the right nanowire/nanosheet part 111, the left nanowire/nanosheet part 110, and the nanogap 125 (with buffer solution 250 in between) together form an FET transistor at block 306. The nanogap 125 is part of the nanopore 109.

At block 308, the ammeter 220 is configured to measure a transistor current (i.e., source to drain current) while a single base (one of the bases 230) of the target molecule 211 is in the nanogap 125 of the nanopore 109, in which the single base 230 affects (e.g., increases) the transistor current.

As compared against an open (nanopore 109) transistor current (when no target molecule 211 is in the nanopore 109 and nanogap 125), an identity of the single base 230 is determined (e.g., visually and/or by a computer analysis) according to a change in the transistor current (e.g., change to the currently measured transistor current via ammeter 220) at block 310. Also, a baseline transistor (nucleotide) current is established for each base such as base A, base G, base C, and base T for a DNA (or RNA) molecule by individually introducing a known base into the system 200 for testing. The measured transistor current via ammeter 220 (for a target molecule 211) is compared against the (known) baseline transistor current (e.g., of base A, G, C, and T) to determine the identity of each single base 230 that traverses through the nanopore 109 and nanogap 125. By analogy, the same analysis is applied for complimentary bases of a double stranded DNA molecule.

The method includes detecting a presence of the target molecule 211 inside the nanogap 125 and the nanopore 109 by a change in ionic current measured by the ammeter 218. The ionic current may decrease when the target molecule 211 is in the nanopore 109 (and nanogap 125), and the voltage of voltage source 219 can be turned on the measure the transistor current via ammeter 220.

The nanowire 105 of the transistor may be at least one of a silicon nanowire, a single carbon nanotube, a multiwall carbon nanotube, and a combination thereof.

The nanosheet 105 of the transistor may be a single layer of graphene, multilayer graphene, or a combination of both. For the nanosheet 105, the multilayer graphene has a thickness ranging from 0.35 nanometers to 10 nanometers. Also, the nanosheet 105 may be at least one of a silicon layer, a polysilicon layer, or a combination of thereof, and the silicon layer has a thickness ranging from 0.35 nanometers to 10 nanometers.

The target molecule 211 may be a single stranded (DNA/RNA) molecule. As such, the distance (separating the left and right parts of the nanowire/nanosheet 105) of the nanogap 125 ranges from 1 nanometer to 2 nanometers in order to detect the transistor current (i.e., source to drain current via ammeter 220) of the single base 230 between the source pad 108 and the drain pad 107 and to confinement movement of the single stranded (DNA/RNA) molecule.

The target molecule 211 may be a double stranded (DNA/RNA) molecule. In this case, the distance (separating the left and right parts of the nanowire/nanosheet 105) of the nanogap 125 ranges from 2 nanometers to 3 nanometers in order to detect the transistor current (i.e., source to drain current via ammeter 220) of complimentary bases between the source pad 108 and the drain pad 107 and to confinement movement of the double stranded molecule.

When the target molecule 211 is a peptide, the single base corresponds to amino acid monomers to be identified.

Figure 4:
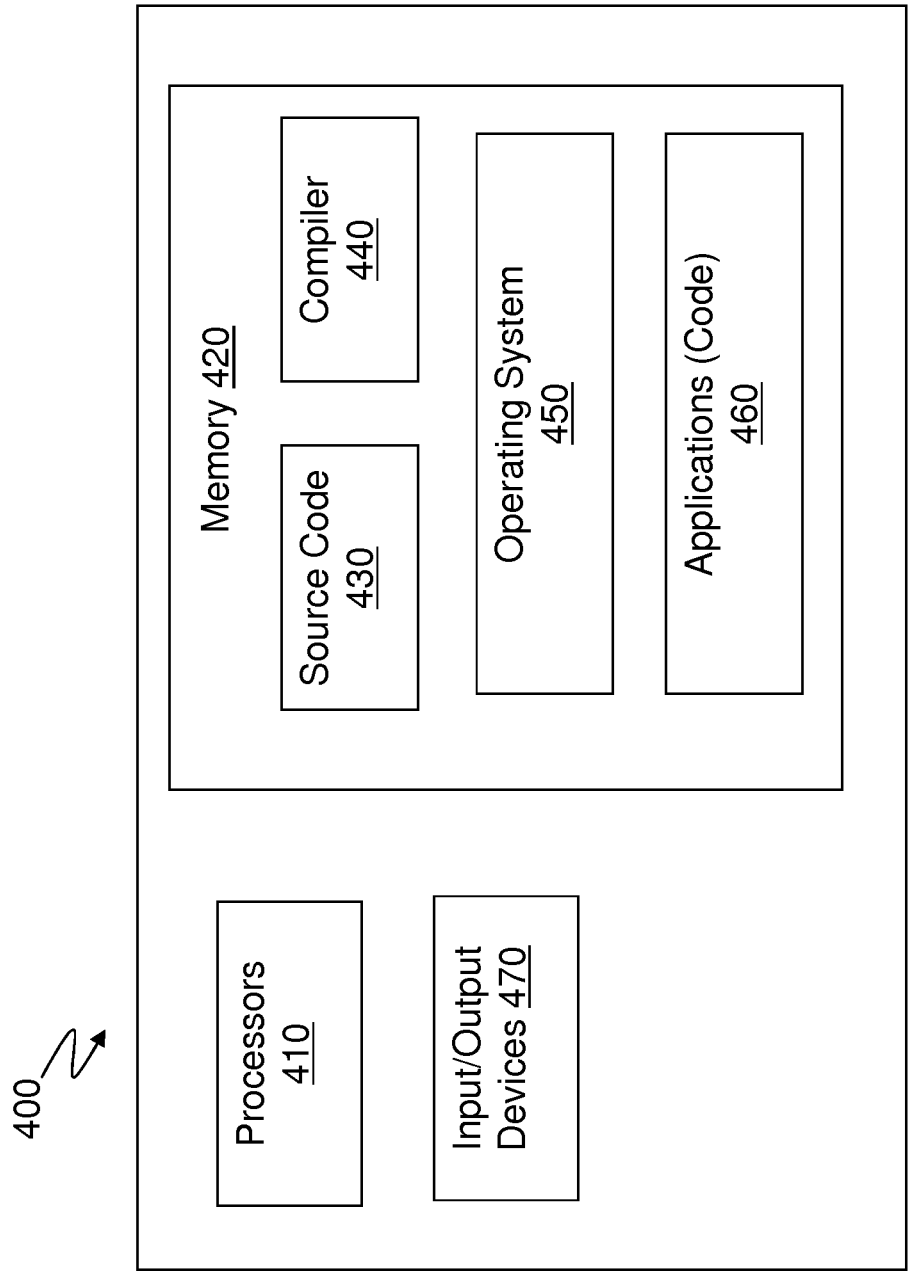
FIG. 4 is a block diagram that illustrates an example of a computer (computer test setup) having capabilities, which may be included in and/or combined with embodiments.

FIG. 4 illustrates an example of a computer 400 (e.g., as part of the computer test setup for testing and analysis) which may implement, control, and/or regulate the respective voltages of the voltage sources, respective measurements of the ammeters, and display screens for displaying various current amplitude (including ionic current and transistor (source to drain current)) as discussed herein. The computer 400 also stores the respective electrical current amplitudes of each base tested and measured to be compared against the baselines current amplitudes of different bases, which is utilized to identify the bases of the tested/target molecule.

Various methods, procedures, modules, flow diagrams, tools, applications, circuits, elements, and techniques discussed herein may also incorporate and/or utilize the capabilities of the computer 400. Moreover, capabilities of the computer 400 may be utilized to implement features of exemplary embodiments discussed herein. One or more of the capabilities of the computer 400 may be utilized to implement, to connect to, and/or to support any element discussed herein (as understood by one skilled in the art) in FIGS. 1-3. For example, the computer 400 which may be any type of computing device and/or test equipment (including ammeters, voltage sources, current meters, connectors, etc.). Input/output device 470 (having proper software and hardware) of computer 400 may include and/or be coupled to the nanodevices and structures discussed herein via cables, plugs, wires, electrodes, patch clamps, etc. Also, the communication interface of the input/output devices 470 comprises hardware and software for communicating with, operatively connecting to, reading, and/or controlling voltage sources, ammeters, and current traces (e.g., magnitude and time duration of current), etc., as discussed and understood herein. The user interfaces of the input/output device 470 may include, e.g., a track ball, mouse, pointing device, keyboard, touch screen, etc., for interacting with the computer 400, such as inputting information, making selections, independently controlling different voltages sources, and/or displaying, viewing and recording current traces for each base, molecule, biomolecules, etc.

Generally, in terms of hardware architecture, the computer 400 may include one or more processors 410, computer readable storage memory 420, and one or more input and/or output (I/O) devices 470 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 410 is a hardware device for executing software that can be stored in the memory 420. The processor 410 can be virtually any custom made or commercially available processor, a central processing unit (CPU), a data signal processor (DSP), or an auxiliary processor among several processors associated with the computer 400, and the processor 410 may be a semiconductor based microprocessor (in the form of a microchip) or a macroprocessor.

The computer readable memory 420 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 420 may incorporate electronic, magnetic, optical, and/or other types of storage media. Note that the memory 420 can have a distributed architecture, where various components are situated remote from one another, but can be accessed by the processor 410.

The software in the computer readable memory 420 may include one or more separate programs, each of which comprises an ordered listing of executable instructions for implementing logical functions. The software in the memory 420 includes a suitable operating system (O/S) 450, compiler 440, source code 430, and one or more applications 460 of the exemplary embodiments. As illustrated, the application 460 comprises numerous functional components for implementing the features, processes, methods, functions, and operations of the exemplary embodiments.

The operating system 450 may control the execution of other computer programs, and provides scheduling, input-output control, file and data management, memory management, and communication control and related services.

The application 460 may be a source program, executable program (object code), script, or any other entity comprising a set of instructions to be performed. When a source program, then the program is usually translated via a compiler (such as the compiler 440), assembler, interpreter, or the like, which may or may not be included within the memory 420, so as to operate properly in connection with the O/S 450. Furthermore, the application 460 can be written as (a) an object oriented programming language, which has classes of data and methods, or (b) a procedure programming language, which has routines, subroutines, and/or functions.

The I/O devices 470 may include input devices (or peripherals) such as, for example but not limited to, a mouse, keyboard, scanner, microphone, camera, etc. Furthermore, the I/O devices 470 may also include output devices (or peripherals), for example but not limited to, a printer, display, etc. Finally, the I/O devices 470 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 470 also include components for communicating over various networks, such as the Internet or an intranet. The I/O devices 470 may be connected to and/or communicate with the processor 410 utilizing Bluetooth connections and cables (via, e.g., Universal Serial Bus (USB) ports, serial ports, parallel ports, FireWire, HDMI (High-Definition Multimedia Interface), etc.).

In exemplary embodiments, where the application 460 is implemented in hardware, the application 460 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. An integrated device for base recognition, the device comprising:
   a nanopore in which to drive a target molecule; and
   a transistor;
   wherein the transistor includes a nanowire or nano sheet separated into a left nanowire part and a right nanowire part to form a nanogap in between, a source pad connected to the right nanowire part, and a drain pad connected to the left nanowire part;
   wherein the nanogap is part of and aligned to the nanopore;
   wherein a transistor current is measured while a single base of the target molecule is in the nanogap of the nanopore, the single base affecting the transistor current; and
   wherein an identity of the single base is determined according to a change in the transistor current.

2. The device of claim 1, wherein the nanowire of the transistor includes at least one of a silicon nanowire, a single carbon nanotube, a multiwall carbon nanotube, and a combination thereof.

3. The device of claim 1, wherein the nanosheet of the transistor includes at least one of a single layer graphene, a multilayer graphene, or a combination of thereof.

* * * * *